United States Patent [19]

Hall

[11] Patent Number: 4,626,548
[45] Date of Patent: Dec. 2, 1986

[54] 7-OXABICYCLOHEPTANE SUBSTITUTED PROSTAGLANDIN COMPOUNDS USEFUL IN THE TREATMENT OF THROMBOTIC DISEASE

[75] Inventor: Steven E. Hall, Ewing Township, Morris County, N.J.

[73] Assignee: E. R. Squibb & Sons, Inc., Princeton, N.J.

[21] Appl. No.: 767,312

[22] Filed: Aug. 19, 1985

[51] Int. Cl.⁴ .................... A61K 31/34; C07D 307/00
[52] U.S. Cl. .................................... 514/469; 549/463
[58] Field of Search ........................ 549/463; 514/469

[56] References Cited
U.S. PATENT DOCUMENTS 4,143,054  3/1979  Sprague ............................... 549/463

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted prostaglandin alcohols are provided having the structural formula

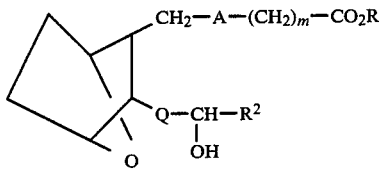

wherein A is —CH=CH— or $(CH_2)_2$; m is 1 to 5; Q is —CH=CH— or $(CH_2)_2$; R is H, alkali metal or alkyl; and $R^2$ is

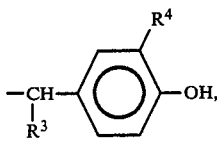

wherein $R^3$ is H or lower alkyl and $R^4$ is H or I and including all steroisomers thereof.

The compounds are cardiovascular agents useful, for example, in the treatment of thrombotic disease.

15 Claims, No Drawings

7-OXABICYCLOHEPTANE SUBSTITUTED PROSTAGLANDIN COMPOUNDS USEFUL IN THE TREATMENT OF THROMBOTIC DISEASE

DESCRIPTION OF THE INVENTION

The present invention relates to 7-oxabicycloheptane substituted prostaglandin compounds which are cardiovascular agents useful, for example, in the treatment of thrombotic disease. These compounds have the structural formula

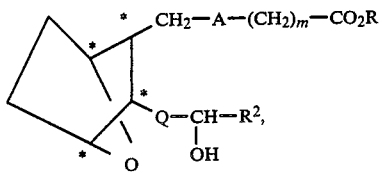

and including all stereoisomers thereof, wherein A is —CH=CH— or $(CH_2)_2$; m is 1 to 8; Q is —CH=CH— or $(CH_2)_2$; and R is H, alkali metal or lower alkyl; $R^2$ is

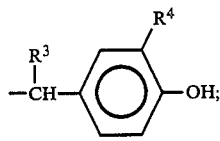

$R^3$ is H or lower alkyl; and $R^4$ is H or I.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclopentyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br, or F), 1 or 2 lower alkoxy groups and/or 1 or 2 hydroxy groups.

The terms "aralkyl", "aryl-alkyl" or "aryl-lower alkyl" as used herein refers to lower alkyl groups as discussed above having an aryl substituent, such as benzyl or methylbenzyl

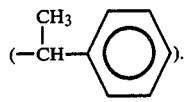

The term "lower alkoxy", "alkoxy" or "aralkoxy" includes any of the above lower alkyl, alkyl or aralkyl groups linked to an oxygen atom.

The term "cycloalkylalkyl" as used herein refers to cycloalkyl groups as defined above linked to an alkyl group as defined above.

The terms "halogen" or "halo" as used herein refers to chlorine, bromine, fluorine or iodine with chlorine being preferred.

The terms "$(CH_2)_m$" and "$(CH_2)_2$" include straight or branched chain radicals having from 1 to 8 carbons in the normal chain in the case of $(CH_2)_m$, and 2 carbons in the normal chain in the case of $(CH_2)_2$, and may contain one or more lower alkyl substituents. Examples of $(CH_2)_m$, and $(CH_2)_2$ groups included $CH_2$,

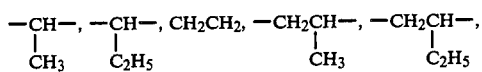

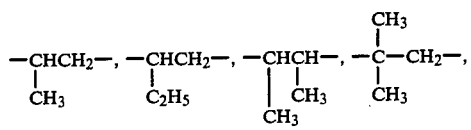

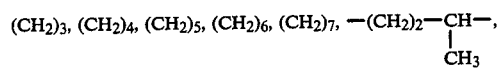

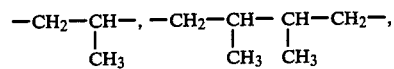

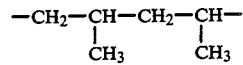

and the like.

Preferred are those compounds of formula I wherein A is —CH=CH— m is 2 to 4, R is H, $R^2$ is

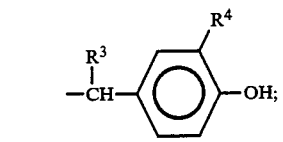

Q is CH=CH, and $R^3$ is lower alkyl and $R^4$ is H or I.

The various comounds of the invention may be prepared as described below.

The compounds of formula I of the invention may be prepared as described below and according to the following reaction sequence.

A. Where A is CH=CH

-continued

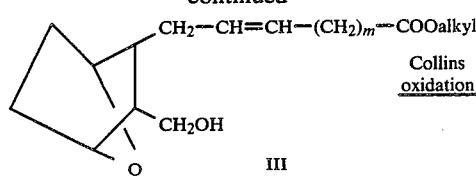
III

Collins oxidation ⟶ 5

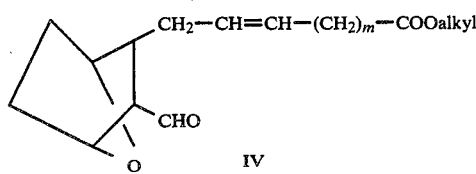
IV

B. Where A is $(CH_2)_2$

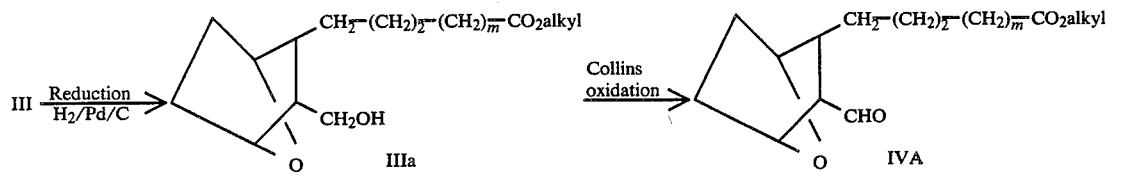

III $\xrightarrow{\text{Reduction} \atop H_2/Pd/C}$ IIIa $\xrightarrow{\text{Collins oxidation}}$ IVA

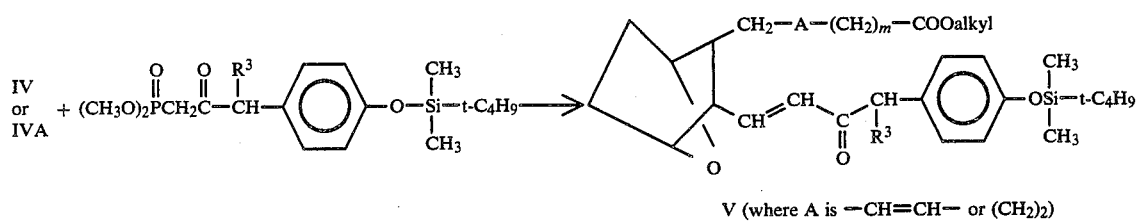

IV or IVA + $(CH_3O)_2\overset{O}{\overset{\|}{P}}CH_2\overset{O}{\overset{\|}{C}}\overset{R^3}{\overset{|}{CH}}$—⟨phenyl⟩—O—Si(CH_3)_2—t-C_4H_9 ⟶

V (where A is —CH=CH— or $(CH_2)_2$)

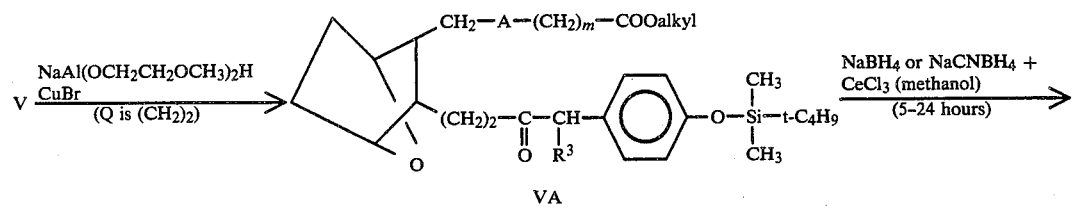

V $\xrightarrow[\text{CuBr}]{NaAl(OCH_2CH_2OCH_3)_2H} \atop (Q is (CH_2)_2)$ VA $\xrightarrow[\text{(5-24 hours)}]{NaBH_4 \text{ or } NaCNBH_4 + CeCl_3 \text{ (methanol)}}$

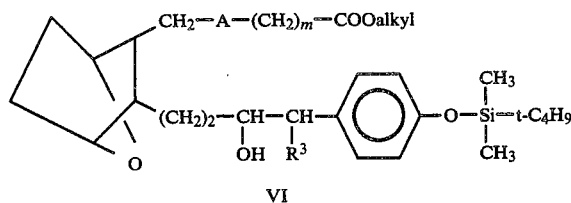
VI

V $\xrightarrow[\text{(Q is —CH=CH—)}]{NaBH_4 + CeCl_3 \text{ (5 to 24 hours)}}$

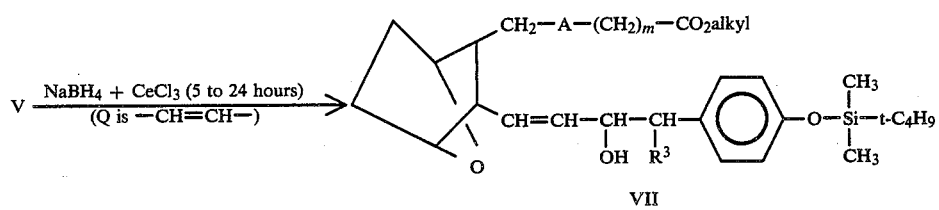
VII

VI, VII $\xrightarrow[\text{LiOH, H}_2\text{O, THF}]{\text{Hydrolysis}}$

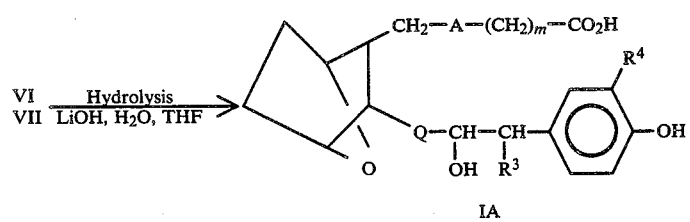
IA

-continued

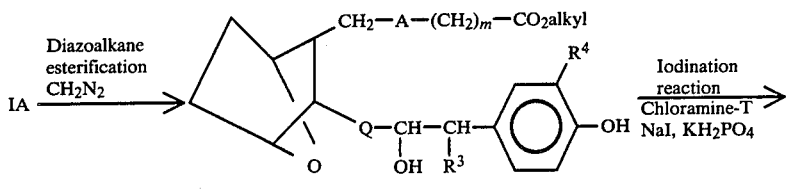

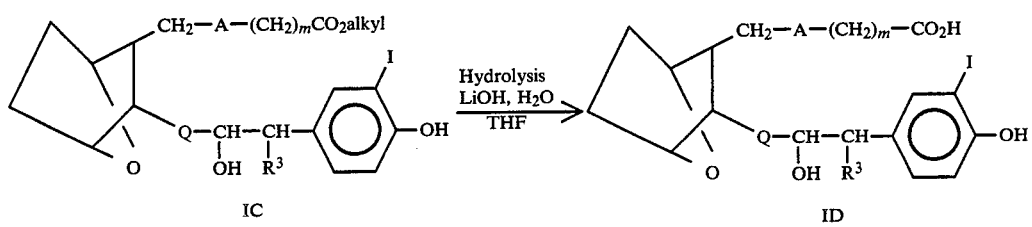

The starting lower alkyl ester containing the hydroxymethyl group (that is, compound III where A is CH=CH— or compound IIIA where A is $(CH_2)_2$— prepared as described in U.S. Pat. No. 4,143,054) is used to form the aldehyde IV or IVA, respectively. Thus, to form aldehyde IV, compound III is subjected to a Collins oxidation, for example, by reacting III with chromium oxide in pyridine. To form aldehyde IVA, compound III is first reduced by treatment with hydrogen in the presence of palladium on charcoal to form IIIA which is subjected to a Collins oxidation as described above to form aldehyde IVA.

Aldehyde IV or IVA of the structure

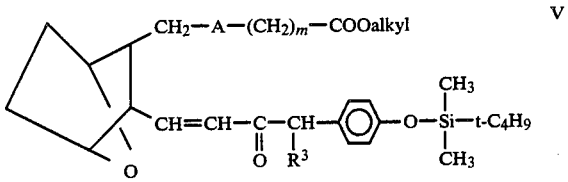

(IV where A is CH=CH—)
IVA where A is $(CH_2)_2$)

is reacted with a dialkoxy phosphonate, such as of the structure

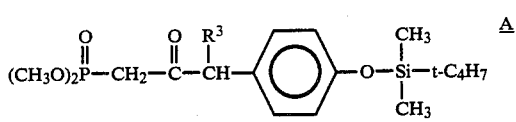

employing a molar ratio of IV or IVA:A of within the range of from about 1:1 to about 0.5:1, under basic conditions, such as in the presence of sodium hydride or lithium diisopropylamide and an inert organic solvent, such as dimethoxyethane (DME), ether, tetrahydrofuran or toluene to form a compound of the structure

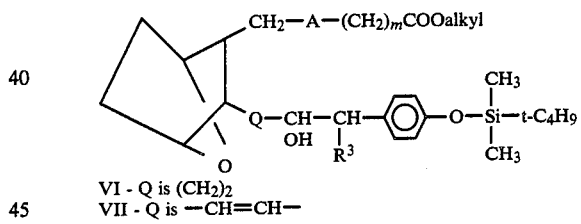

Compound V may then be reduced by two different ways as outlined above to form compounds VI or VII

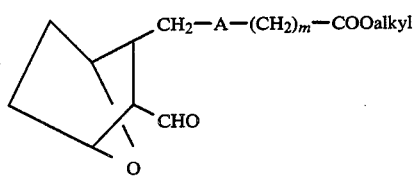

VI - Q is $(CH_2)_2$
VII - Q is —CH=CH—

Thus, to form compound VI wherein Q is $(CH_2)_2$, compound V is first reacted with $NaAl(OCH_2CH_2OCH_3)_2H$ in the presence of CuBr and then the reaction product is reduced, for example, by treating with a reducing agent such as sodium borohydride or sodium cyanoborohydride in a solvent such as methanol and in the presence of cerium trichloride for a period of from about 5 to about 24 hours to form the compound of formula VI

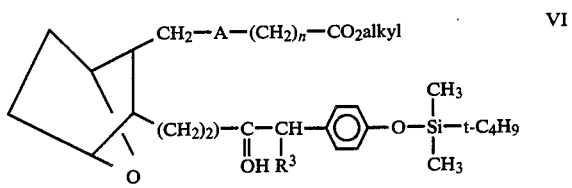

To form compound VII (where Q is CH=CH), ester V is reduced using sodium borohydride or sodium cyanoborohydride and cerium trichloride as described above to form the compound of formula VII

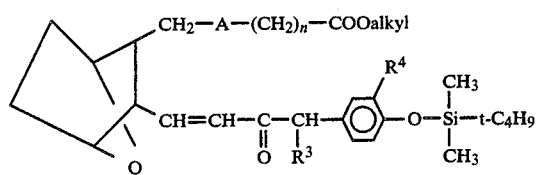  VII

Ester VI and VII may be hydrolyzed by reaction with lithium hydroxide, potassium carbonate or sodium hydroxide in the presence of an inert organic solvent such as tetrahydrofuran, methanol or dimethoxyethane-water to form acid compounds of the invention IA.

Compounds of formula I wherein $R^4$ is I may be prepared from compound IA by esterifying IA with a diazoalkane such as diazomethane to form the ester IB. Ester IB is then subjected to an iodination reaction wherein a solution of ester IB in methanol is treated with $KH_2PO_4$ buffer (pH~7.5), sodium iodide and the oxidizing agent Chloramine-T hydrate in $KH_2PO_4$ buffer to form the iodinated ester IC which may be hydrolyzed as described hereinbefore to form the iodinated acid ID.

The starting dialkoxy phosphate A wherein $R^3$ is alkyl may be prepared by treating phenol B

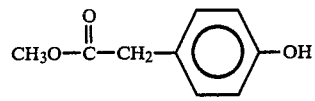 B with t-butyl dimethylsilyl chloride in the presence of imidazole in inert organic solvent such as dimethylformamide under argon to form the silyl compound C

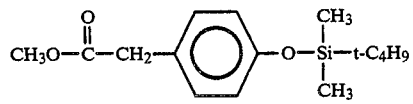 C which is alkylated by treating a solution of silyl compound C in tetrahydrofuran with a solution of diisopropylamine in tetrahydrofuran containing n-butyllithium in hexane. Thereafter alkylating agent D Alkyl-Hal    D wherein Hal is Cl, I or Br is added to form the akylated silyl compound E

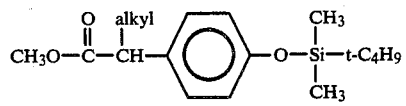 E

Compound E is then condensed with phosphorus compound F

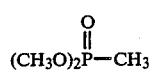 F in the presence of n-butyllithium to form the dialkoxy phosphate reactant A.

Where $R^3$ is H, then silyl compound C may be directly condensed with phosphorus compound F to form the dialkoxy phosphate A'

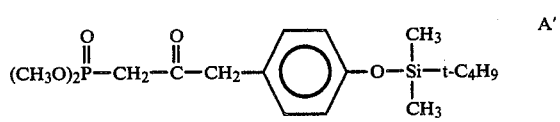 A'

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo-, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

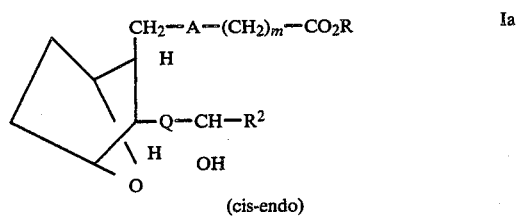 Ia (cis-endo)

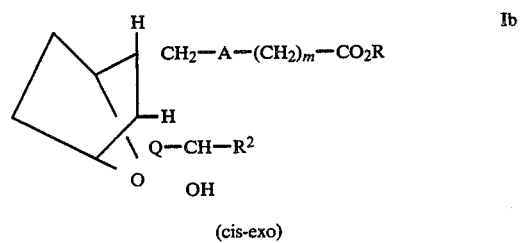 Ib (cis-exo)

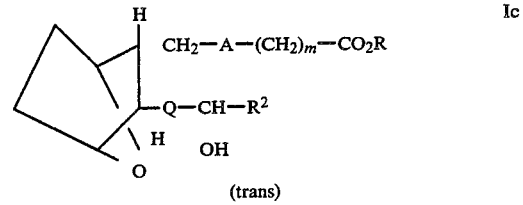 Ic (trans)

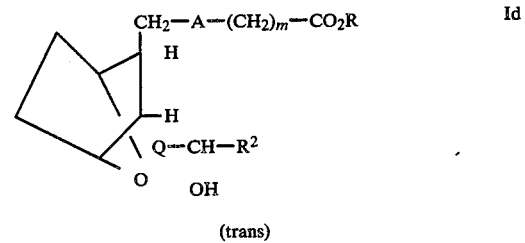 Id (trans)

The wavy line ( ) in the above formulae indicates that the hydroxy group in each of the compounds of the formulae Ia–Id is either R($\beta$) or S($\alpha$).

The nucleus in each of the compounds of the invention is depicted as

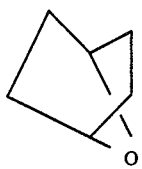

for matter of convenience; it will also be appreciated that the nucleus in the compounds of the invention may be depicted as

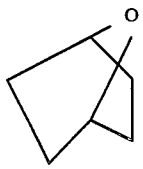

The compounds of this invention are cardiovascular agents useful as platelet aggregation inhibitors, such as inhibiting arachidonic acid-induced platelet aggregation (e.g., for treatment of thrombotic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of myocardial ischemic disease, such as angina pectoris.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1S-[1α,2β(Z),3β(1E,3R,4S),4α]-7-[3-[3-Hydroxy-4-(4-hydroxyphenyl)-1-pentenyl]-7-oxabicyclo[2.2.1]hept-2-yl]-5-heptenoic acid A. Dimethyl 3-[4-(t-Butyldimethylsiloxy)phenyl]-2-oxo-butylphosphonate A(1) Methyl4-(t-butyldimethylsiloxy)phenyl acetate A solution of 10.0 g of methyl 4-hydroxy phenyl acetate (60.2 mmol), 8.6 g of imidazole (126 mmol) in 50 ml of dry DMF under Ar was cooled to 0° C. To this stirred solution was added 9.5 g (63 mmol) of t-butyl dimethylsilyl chloride. The reaction mixture was allowed to warm to room temperature and stirred at room temperature for 2 days. The reaction mixture was then partitioned between 500 ml each of $H_2O$ and 2:1 hexane-ether. The aqueous layer was extracted with 400 ml of 2:1 hexane-ether. The combined organic extracts were washed with 300 ml $H_2O$, dried over $MgSO_4$, filtered, and concentrated in vacuo to afford 17.0 g of crude product. Bulb-to-bulb distillation of 16.5 g (oven setting 160° C., 2–5 mm Hg) to afford 15.4 g of title ester in the form of a water-white slightly viscous liquid.

A(2) Methyl 2-[4-(t-butyldimethylsiloxy)phenyl]propionate

To a cooled (−78° C.) solution of 6.0 ml of diisopropylamine (42.8 mmol) in 200 ml of THF was added dropwise over 25 minutes 23.0 ml of 1.57M nBuLi/hexane (36.11 mmol). This solution was stirred at −78° C. for 35 minutes at which time the addition of a solution of 10.0 g of Part A(1) ester (35.7 mmol) in 60 ml of THF was begun. This addition was complete in 50 minutes. The reaction mixture was stirred for an additional 35 minutes and then 8.0 ml (128 mmol) of $CH_3I$ was added over approximately one minute. Ten minutes later the cold bath was removed and the mixture was allowed to warm to room temperature overnight.

The mixture was partitioned between 400 ml ether and 300 ml of 0.1N HCl. The ether layer was washed with 200 ml of saturated $NaSO_3$. The ether layer was dried over $MgSO_4$, filtered and concentrated in vacuo to 11.4 g crude product. Purification was effected by bulb-to-bulb distillation (oven setting 160° C., 2–5 mm Hg) to given 10.4 g (99%) of pure title ester.

A(3) Dimethyl 3-[4-(t-butyldimethylsiloxy)phenyl]-2-oxo-butylphosphonate

To a stirred solution of 1.17 ml (10.8 mmol) of $(MeO)_2P(O)CH_3$ in 6 ml of THF at −78° C. was added dropwise 5.0 ml of 1.57M nBuLi/hexane over a period of 10 minutes. Thirty-five minutes later an additional 1 ml of THF was added (to thin out slurry) followed by the addition of a solution of 0.9 ml Part A(2) ester in 2 ml of THF and rinsed in with 3 ml of THF. After 2 hours, the reaction had warmed to 0° C. The reaction was quenched by the addition of 0.6 ml of HOAc in 1 ml of THF and stored overnight in the refrigerator.

The following day the mixture was concentrated in vacuo. The residue was partitioned between 40 ml of saturated $NaHCO_3$ and ether. The aqueous layer was extracted with 30 ml of ether. The combined ether layers were washed with 30 ml saturated NaCl. The brine wash was back-extracted with 30 ml of ether. The combined ether layers were dried over $MgSO_4$, filtered, and concentrated in vacuo to afford 1.25 g of crude product. Bulb-to-bulb distillation (oven setting 240° C., 2–5 mm Hg) afforded 0.99 g of title phosphonate (84%).

B. [1S-[1α,2β(5Z),3β(1E),4α]]-7-[3-[3-Oxo-4-(4-t-butyldimethylsiloxyphenyl)-1-pentenyl-7-oxabicyclo[2.2.1]hept-2-yl]-5-heptenoic acid, methyl ester To a thoroughly dried flask containing 236 mg (2.71 mmol) of anhydrous LiBr was added a solution of 930 mg (2.41 mmol) of phosphonate in 5 ml of $CH_2Cl_2$. To this stirred slurry was added 0.33 ml (2.38 mmol) of Et₃N. This slurry was stirred for 40 minutes at room temperature and then a solution of 475 mg of optically active [1α,2β(5Z),3β,4α]-7-[3-formyl-7-oxabicyclo[2.2.1]-hept-2-yl]-5-heptenoic acid, methyl ester prepared from the corresponding hydroxy methyl compound (III) (as described in U.S. Pat. No. 4,143,054), 1.79 mmol, in 5 ml of CH₂Cl₂ was added dropwise over 5 minutes. The reaction mixture was stirred at room temperature overnight and then partitioned between 25 ml each of EtOAc and 0.1N HCl. The EtOAc layer was washed with 25 ml saturated NaHCO₃. Separation of the layers was difficult so an additional 20 ml of EtOAc was added. The organic layer was dried over MgSO₄, filtered and concentrated in vacuo to give 1.12 g of crude enone. Purification was effected by flash chromatography on 40 g of silica gel using 2:1 hexane-ether as eluant. Fractions 23-55 were concentrated in vacuo to give 0.85 g (90%) of an approximated 55:45 mixture of title enone. TLC: silica gel, 2% MeOH/CH₂Cl, $R_f$=0.7, Ce(SO₄)₂.

C.
[1S-[1α,2β(5Z),3β(1E,3R,4S),4α]]-7-[3-[3-hydroxy-4-(4-t-butyldimethylsiloxyphenyl)-1-pentenyl]-7-oxobicyclo[2.2.1]-hept-2-yl]-5-heptenoic acid, methyl ester and

D.
[1S-[1α,2β(5Z),3β(1E,3R,4R),4α]]-7-[3-[3-hydroxy-4-(4-t-butyldimethylsiloxyphenyl)-1-pentenyl]-7-oxabicyclo[2.2.1]-hept-2-yl]-5-heptenoic acid, methyl ester To a stirred solution of 800 mg Part B enone (1.52 mmol) in 3 ml of MeOH and 3 ml of THF was added 550 mg of CeCl₃.7H₂O. This was stirred at room temperature for 10 minutes and then cooled to −50° C. To this solution was added 65 mg (1.71 mmol) of NaBH₄ in one amount. The reaction mixture was stirred for 2.25 hours, allowing the bath temperatures to warm to −30° C. On re-cooling to −50° C., the reaction mixture was quenched by the addition of 2 ml of pre-chilled acetone. After stirring an additional 25 minutes, the mixture was concentrated in vacuo. The residue was partitioned between 40 ml of ether and 20 ml of 1N HCl. The aqueous layer was extracted with 20 ml of ether. The combined ether layers were washed with 30 ml H₂O, dried over NaHCO₃/MgSO₄ and concentrated in vacuo to afford 0.75 g of colorless oil. This was chromatographed on 40 g of silica gel using 1% MeOH/CH₂Cl₂ as eluant. Fractions 36-39 afforded 160 mg of pure title C fast moving isomer (FMI). Fractions 40-43 gave a mixture of Part C and D fast moving isomers (230 mg).

TLC: silica gel 2% MeOH/CH₂Cl₂, $R_f$=0.39 (FMI-C), 0.33 (FMI-D).

E.
[1S-[1α,2β(5Z),3β(1E,3R,4S),4α]]-7-[3-[3-hydroxy-4-(4-hydroxyphenyl)-1-pentenyl]-7-oxabicyclo[2.2.1]-hept-2-yl]-5-heptenoic acid To a stirred solution of 160 mg (0.30 mmol) of Part C alcohol in 4.0 ml of THF and 1.0 ml of H₂O was added 2.0 ml of 1N LiOH solution. The mixture was purged with a stream of Ar for 5 minutes and then stirred at room temperature for 4.5 hours. The mixture was diluted with 10 ml saturated NaCl, acidified to pH=3, and extracted with three 20 ml portions of ether. The combined ether layers were dried over MgSO₄, filtered, and concentrated in vacuo. The crude product was chromatographed on 27 g of silica gel using 6% MeOH/CH₂Cl₂ as eluant to afford 90 mg (74%) of title acid. [α]$_D$=+50.4 (c=1, CHCl₃).

TLC: silica gel, 6% MeOH/CH₂Cl₂, $R_f$=0.4, Ce(SO₄)₂.

Anal Calcd for C₂₄H₃₂O₅: C, 72.00; H, 8.05. Found: C, 71.77; H, 8.12.

EXAMPLE 2

[1S-[1α,2β(5Z),3β(1E,3R,4S),4α]-7-[3-[3-Hydroxy-4-(4-hydroxy-3-iodophenyl)-1-pentenyl]-7-oxabicyclo[2.2.1]hept-2-yl]-5-heptenoic acid

A.
[1S-[1α,2β(5Z),3α(1E,3R,4S),4α]-7-[3-[3-Hydroxy-4-(4-hydroxy-3-iodophenyl)-1-pentenyl]-7-oxabicyclo[2.2.1]hept-2-yl]-5-heptenoic acid, methyl ester To a 0° C. solution of 200 mg of Example 1 acid in 1 ml of CH₃OH was added dropwise etheral CH₂N₂ until the yellow color presisted. Concentration in vacuo afforded title A ester.

B.
[1S-[1α,2β(5Z),3β(1E,3R,4S),4α]-7-[3-[3-Hydroxy-4-(4-hydroxy-3-iodophenyl)-1-pentenyl]-7-oxabicyclo[2.2.1]hept-2-yl]-5-heptenoic acid, methyl ester and

C.
[1S-[1α,2β(5Z),3β(1E,3R,4S),4α]-7-[3-[3-Hydroxy-4-(3,5-diiodo-4-hydroxyphenyl)-1-pentenyl]-7-oxabicyclo[2.2.1]hept-2-yl]-5-heptenoic acid, methyl ester To a stirred solution of 210 mg (0.51 mmol) of Part A ester in 30 ml of CH₂OH was added 70 ml of 0.5M KH₂PO₄ buffer (pH=7.5). This caused the evolution of some heat so the flask was immersed in an ice bath until the contents were slightly cooled (15°-20° C.). To this stirred mixture was added 88 mg (0.59 mmol) of NaI followed by a solution of 436 mg (1.92 mmol) of Chloramine-T hydrate in 50 ml of 0.5M KH₂PO₄ buffer. The mixture was stirred for an additional 90 seconds and then quenched by the addition of 9 ml of saturated Na₂S₂O₅ solution. This was extracted with three 150 ml portions of CH₂Cl₂. The combined CH₂Cl₂ layers were dried over MgSO₄, filtered, and concentrated in vacuo to afford the crude product. Purification was effected by chromatography on 40 g of silica gel using 2% MeOH/CH₂Cl₂ as eluant. This gave 90 mg of impure title B diiodide, 184 mg of impure title C iodide and 92 mg (44%) of recovered starting Part A ester.

TLC: silica gel, 2% CH₃OH/CH₂Cl₂, $R_f$: 2 (0.25), 3 (0.37).

The 92 mg of recovered Part A ester was subjected to the above reaction. Thus the total of Parts B and C compounds after one recycle was 160 mg and 271 mg respectively. Both of these compounds were contaminated with varying amounts of p-toluene sulfonamide.

D.
[1S-[1α,2β(5Z),3β(1E,3R,4S),4α]-7-[3-[3-Hydroxy-4-(4-hydroxy-3-iodophenyl)-1-pentenyl]-7-oxabicyclo[2.2.1]-hept-2-yl]-5-heptenoic acid To a stirred solution of 184 mg impure Part C iodide in 4 ml of THF was added 1.0 ml of H₂O followed by 2.0 ml of 1N LiOH solution. This mixture was purged with a stream of argon for 10 minutes. Analysis of the reaction by TLC showed it to be complete after 3 hours. The reaction mixture was partitioned between 25 ml each brine and EtOAc. The aqueous layer was acidified to pH~3.5 by the addition of 1N HCl. The aqueous layer was extracted with two 35 ml portions of EtOAc. The combined organic layers were dried over MgSO4, filtered and concentrated in vacuo. Purification was effected by chromatography on 30 g of silica gel using 4% CH3OH/CH2Cl2 as eluant to afford 88 mg of pure title iodide (33% overall from the Part A ester).

Another portion of impure Part C iodide (87 mg) was hydrolyzed under the same conditions. Purification of the acid was efected by prep TLC (20×20 cm, 0.5 mm thick) using 4% MeOH/CH2Cl2. Elution of the compound from the silica gel with EtOAc and 6% MeOH/CH2Cl2 afforded 36 mg of pure title iodide. These two amounts were combined. Thus, the overall yield of Part A ester to title mono-iodo acid was 46%. TLC: silica gel, 4% CH3OH/CH2Cl2, $R_f$=0.30, I2.

Anal Calcd for $C_{24}H_{31}O_5I$: C, 54.75; H, 5.94; I, 24.11. Found: C, 54.82; H, 5.99; I, 24.04.

EXAMPLE 3

[1S-1α,2β(Z),3β(4S),4α]-7-[3-[3-Hydroxy-4-(4-hydroxyphenyl)-1-pentyl]-7-oxabicyclo[2.2.1]hept-2-yl-5-heptenoic acid

A.

[1S-[1α,2β(Z),3β(4S),4α]]-7-[3-[3-Oxo-4-(4-t-butyldimethylsilyloxyphenyl)-1-pentyl]-7-oxabicyclo[2.2.1]-hept-2-yl]-5-heptenoic acid, methyl ester To a suspension of 686 mg of purified cuprous bromide (4.8 mmole) in 12 ml of dry THF, cooled at 0°-5° C. is added with stirring 1.35 ml of a 3.5M solution of red-Al (sodium bis(2-methoxyethoxy)aluminumhydride) in toluene dropwise. The solution is stirred at 0°-5° C. for 30 minutes, whereupon it is cooled to −78° C. and 2 ml of n-butanol (18 mmole) is added rapidly, followed by a solution of Example 1 Part B enone (1.2 mmole) in 4 ml of dry THF. After 10 minutes at −78° C., the reaction mixture is warmed to −20° C. and left for an additional one hour. The reaction mixture is quenched by addition of 70 ml of water and then poured into saturated ammonium chloride solution and is extracted with ether (×3). The ether extract was dried over anhydrous magnesium sulfate, filtered and the filtrate was concentrated under reduced pressure to yield desired title ketone.

B.

[1S-[1α,2β(Z),3β(4S),4α]-7-[3-[3-Hydroxy-4-(4-hydroxyphenyl)-1-pentyl]-7-oxabicyclo[2.2.1]hept-2-yl]-5-heptenoic acid Following the procedure of Example 1 except substituting the Part A enone for the Example 1 Part B enone, the title compound is obtained.

EXAMPLE 4

(1α,2β,3β,4α)-7-[3-[3-Hydroxy-4-(4-hydroxyphenyl)-1-pentyl]-7-oxabicyclo[2.2.1]hept-2-yl]heptanoic acid

A.

(1α,2β,3β,4α)-7-[3-(Hydroxymethyl)-7-oxabicyclo[2.2.1]hept-2-yl]-heptanoic acid, methyl ester To 800 mg (3.0 mmol) of the [1α,2β(Z),3β,4α]-7-[3-(hydroxymethyl)-7-oxabicyclo[2.2.1]-hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

[1α,2β,3β(4S),4α]-7-[3-[3-Oxo-4-(4-t-butyldimethylsilyloxyphenyl)-1-pentenyl]-7-oxabicyclo[2.2.1]hept-2-yl]heptanoic acid, methyl ester Following the procedure of Example 1 Part B except substituting the Part A alcohol-ester for the alcohol ester (or aldehyde) used in Example 1, Part B, the title enone is obtained.

C.

[1α,2β,3β(4S),4α]-7-[3-[3-Oxo-4-(4-t-butyldimethylsilyloxyphenyl)-1-pentyl]-7-oxabicyclo[2.2.1]hept-2-yl]heptanoic acid, methyl ester To a suspension of 686 mg of purified cuprous bromide (4.8 mmole) in 12 ml of dry THF, cooled at 0°-5° C. is added with stirring 1.35 ml of a 3.5M solution of red-Al (sodium bis(2-methoxyethoxy)aluminumhydride) in toluene dropwise. The solution is stirred at 0°-5° C. for 30 minutes, whereupon it is cooled to −78° C. and 2 ml of n-butanol (18 mmol) is added rapidly, followed by a solution of 476 mg of the title B enone (1.2 mmole) in 4 ml of dry THF. After 10 minutes at −78° C., the reaction mixture is warmed to −20° C. and left for an additional one hour. The reaction mixture is quenched by addition of 70 ml of water and then poured into saturated ammonium chloride solution and was extracted with ether (×3). The ether extract is dried over anhydrous magnesium sulfate, filtered and the filtrate is concentrated under reduced pressure. 478 mg of desired title ketone is obtained (100% yield) as a colorless oil.

D.

[1α,2β,3β(4S),4α]-7-[3-[3-Hydroxy-4-(4-hydroxyphenyl)-1-pentyl]-7-oxabicyclo[2.2.1]hept-2-yl]heptanoic acid Following the procedure of Example 1 except substituting the above title C enone for the Example 1 Part B enone, the title compound is obtained.

EXAMPLES 5 TO 8

Following the procedures outlined in the specification and described in the working Examples, the following additional compounds in accordance with the present invention may be prepared.

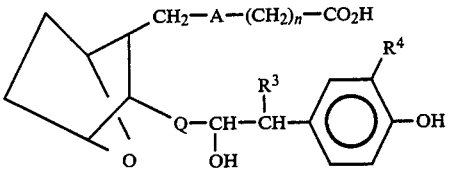

| Ex. No. | A | (CH2)n | Q | R3 | R4 |
|---|---|---|---|---|---|
| 5. | CH=CH— | (CH2)2 | (CH2)2 | C3H7 | H |
| 6. | CH=CH | (CH2)4 | CH=CH | C6H13 | I |
| 7. | CH=CH— | (CH2)5 | (CH2)2 | C2H5 | I |
| 8. | CH=CH— | (CH2)2 | CH=CH | C6H5 | H |
| 9. | CH=CH— | (CH2)3 | (CH2)2 | CH3 | I |
| 10. | (CH2)2 | CH2 | CH=CH | H | I |
| 11. | (CH2)2 | (CH2)3 | (CH2)2 | H | H |
| 12. | (CH2)2 | (CH2)2 | CH=CH | H | H |
| 13. | (CH2)2 | (CH2)3 | CH=CH | H | H |
| 14. | (CH2)2 | (CH2)3 | (CH2)2 | CH3— | I |

-continued

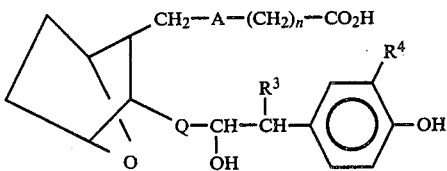

| Ex. No. | A | $(CH_2)_n$ | Q | $R^3$ | $R^4$ |
|---|---|---|---|---|---|
| 15. | $(CH_2)_2$ | $(CH_2)_3$ | CH=CH | $CH_3—$ | I |
| 16. | CH=CH | $—CH_2$ | $(CH_2)_2$ | $CH_3—$ | I |
| 17. | CH=CH— | $(CH_2)_5$ | CH=CH | $C_4H_9$ | H |
| 18. | $(CH_2)_2$ | $(CH_2)_7$ | $(CH_2)_2$ | $C_5H_{11}$ | I |

What is claimed is:

1. A compound having the structural formula

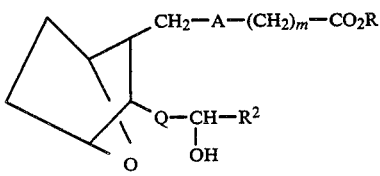

and including all stereoisomers thereof, wherein A is —CH=CH— or $(CH_2)_2$; m is 1 to 5; Q is —CH=CH— or $(CH_2)_2$; R is H, alkali metal or alkyl; and and $R^2$ is

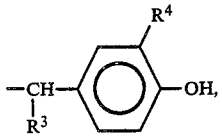

$R^3$ is H or lower alkyl and $R^4$ is H or I, wherein lower alkyl or alkyl alone or as part of another group contains 1 to 12 carbons and is unsubstituted or is substituted with halo, $CF_3$, alkoxy, aryl, alkyl-aryl, haloaryl, cycloalkyl or alkylcycloalkyl;

aryl alone or as part of another group is phenyl or naphthyl which is unsubstituted or is substituted with 1 or 2 lower alkyl groups, 1 or 2 halogens, 1 or 2 hydroxy groups and/or 1 or 2 lower alkoxy groups;

cycloalkyl alone or as part of another group contains 3 to 12 carbons and is unsubstituted or is substituted with 1 or 2 halogens, 1 or 2 lower alkyl groups and/or 1 or 2 lower alkoxy groups;

$(CH_2)_m$ or $(CH_2)_2$ may contain 1 or 2 lower alkyl substituents.

2. The compound as defind in claim 1 wherein A is —CH=CH—, m is 1 to 5, and Q is CH=CH.

3. The compound as defined in claim 1 wherein A is $(CH_2)_2$, and Q is CH=CH.

4. The compound as defined in claim 1 wherein and A is $(CH_2)_2$ and Q is $(CH_2)_2$.

5. The compound as defined in claim 1 wherein $R^3$ is alkyl.

6. The compound as defined in claim 1 wherein $R^4$ is H.

7. The compound as defined in claim 1 wherein $R^4$ is I.

8. The compound as defined in claim 1 wherein $R^3$ is $CH_3$, $R^4$ is I or H.

9. The compound as defined in claim 1 having the name [1α,2β(Z),3β(1E,3R,4S),4β]-7-[3-[3-hydroxy-4-(4-hydroxyphenyl)-1-pentenyl]-7-oxabicyclo[2.2.1]hept-2-yl]-5-heptenoic acid, including all stereoisomers thereof.

10. The compound as defined in claim 1 having the name [1S-[1α,2β(Z),3β(1E,3R,4S),4α]-7-[3-[3-hydroxy-4-(4-hydroxy-3-iodophenyl)-1pentenyl]-7-oxabicyclo[2.2.1]-hept-2-yl]-5-heptenoic acid.

11. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier thereof.

14. A method of inhibiting bronchoconstriction associated with asthma, which comprises administering to a mammalian host an effective amount of a compound as defined in claim 1 or a pharmaceutically acceptable salt thereof.

15. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,626,548

DATED : December 2, 1986

INVENTOR(S) : Steven E. Hall

It is certified that error appears in the above-identified patent and that said Letters Patent is hereby corrected as shown below:

Column 1, line 52, "cyclopentyl", second occurrence, should read --cyclohexyl--.

Column 6, line 60, structure VI should read

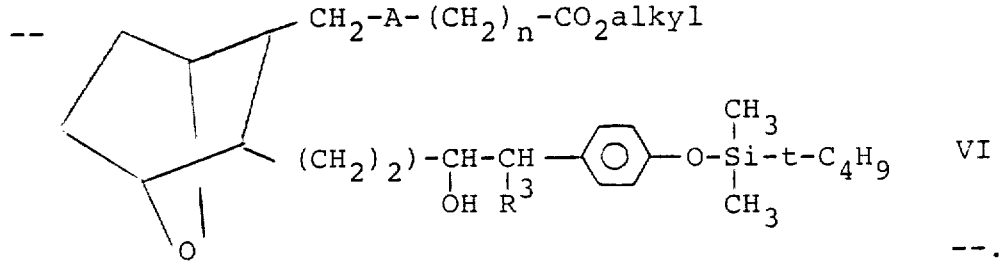

Column 7, line 1, structure VII should read

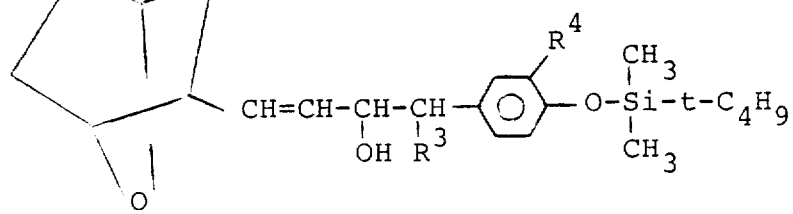

UNITED STATES PATENT AND TRADEMARK OFFICE
CERTIFICATE OF CORRECTION

PATENT NO. : 4,626,548

DATED : December 2, 1986

INVENTOR(S) : Steven E. Hall

It is certified that error appears in the above-identified patent and that said Letters Patent is hereby corrected as shown below:

Column 8, lines 25-60, structures Ia, Ib, Ic and Id should read as follows:

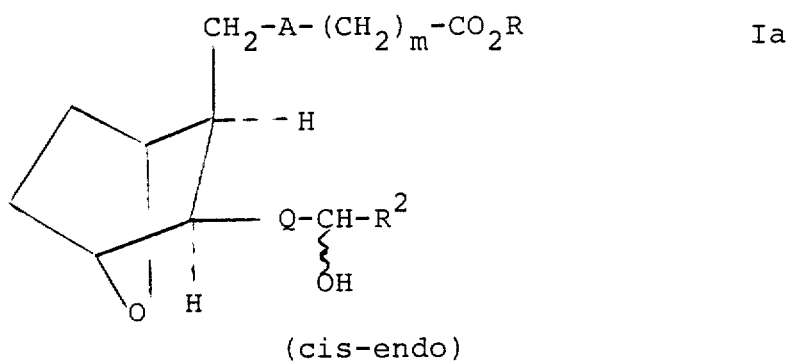

(cis-endo)    Ia

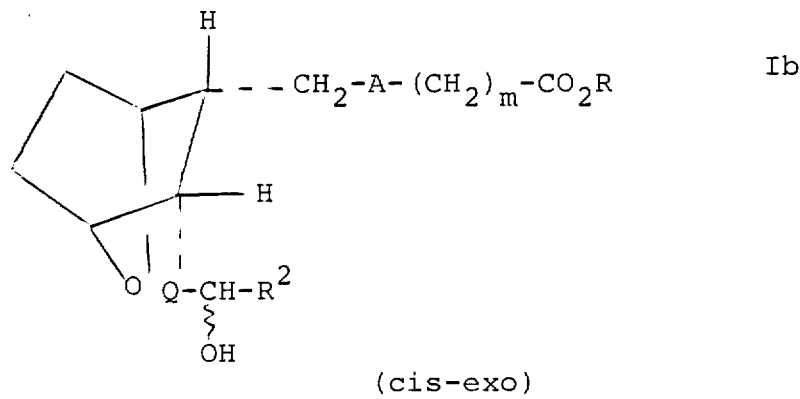

(cis-exo)    Ib

UNITED STATES PATENT AND TRADEMARK OFFICE
CERTIFICATE OF CORRECTION

PATENT NO. : 4,626,548

DATED : December 2, 1986

INVENTOR(S) : Steven E. Hall

It is certified that error appears in the above-identified patent and that said Letters Patent is hereby corrected as shown below:

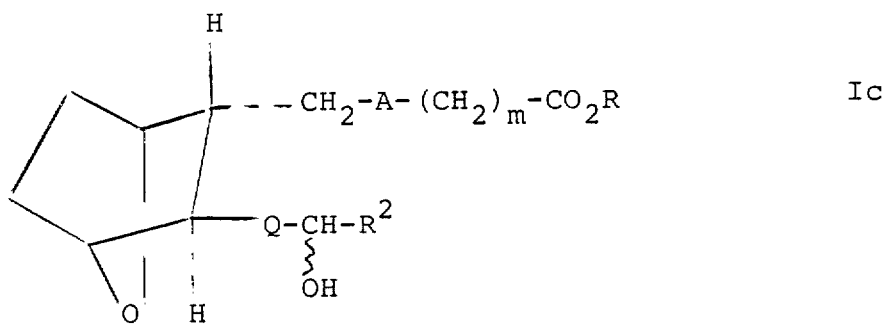

Ic (trans)

UNITED STATES PATENT AND TRADEMARK OFFICE
CERTIFICATE OF CORRECTION

PATENT NO. : 4,626,548

DATED : December 2, 1986

INVENTOR(S) : Steven E. Hall

It is certified that error appears in the above-identified patent and that said Letters Patent is hereby corrected as shown below:

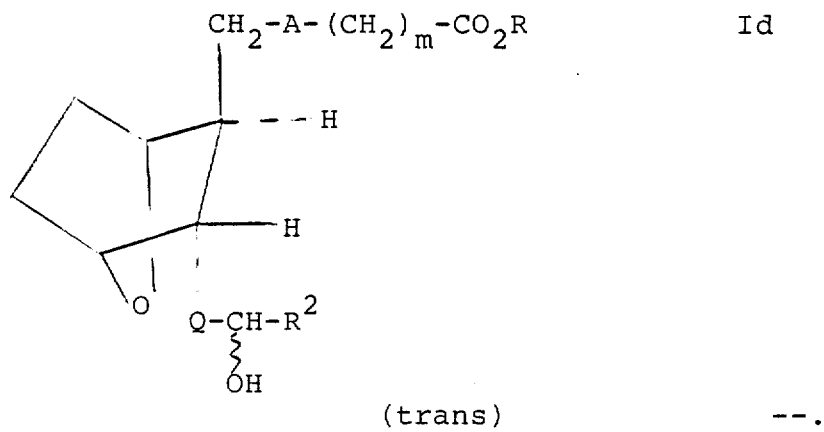

Column 8, line 64, "wavy line ( )" should read
--wavy line (∫)--.

Signed and Sealed this

Twenty-fourth Day of March, 1987

Attest:

DONALD J. QUIGG

Attesting Officer    Commissioner of Patents and Trademarks